US00PP34510P2

(12) United States Plant Patent
Stock et al.

(10) Patent No.: US PP34,510 P2
(45) Date of Patent: Aug. 16, 2022

(54) ***ASPARAGOPSIS TAXIFORMIS* PLANT NAMED 'ICARUS'**

(50) Latin Name: *Asparagopsis taxiformis*
Varietal Denomination: Icarus

(71) Applicant: Symbrosia, Inc., Kailua-Kona, HI (US)

(72) Inventors: Daisy Stock, Kailua-Kona, HI (US); Alexia Akbay, Kailua-Kona, HI (US); Claire Goloja, Waconia, MN (US)

(73) Assignee: Symbrosia, Inc., Kailua-Kona, HI (US)

( * ) Notice: Subject to any disclaimer, the term of this patent is extended or adjusted under 35 U.S.C. 154(b) by 0 days.

(21) Appl. No.: 17/300,781

(22) Filed: Nov. 4, 2021

(51) Int. Cl.
*A01H 13/00* (2006.01)

(52) U.S. Cl.
USPC ..... Plt./395

(58) Field of Classification Search
USPC ..... Plt./395
See application file for complete search history.

(56) References Cited

U.S. PATENT DOCUMENTS 9,980,995 B2 5/2018 Machado et al.

FOREIGN PATENT DOCUMENTS

WO WO 2015/109362 A2 7/2015

OTHER PUBLICATIONS

[No Author Listed] *Asparagopsis taxiformis*. Wikipedia, https://en.wikipedia.org/wiki/Asparagopsis_taxiformis [last edited Dec. 19, 2021; last accessed Jan. 4, 2022].

*Primary Examiner* — Annette H Para

(74) *Attorney, Agent, or Firm* — Wolf, Greenfield & Sacks, P.C.

(57) ABSTRACT

A new and distinct cultivar of the red macroalgae *Asparagopsis taxiformis* named "Icarus," characterized by significantly smaller internal branching angles, a smaller form when aggregated in tumble culture, and a dark red pigmentation. New branches of this macroalgae are generated prolifically at higher temperatures than wild-type *A. taxiformis*, making "Icarus" well-suited for commercial growth, e.g., when there is a risk of extreme heat events, in cases of needing to lower the cost of cooling cultivars, or other such conditions.

3 Drawing Sheets

Figure 1:
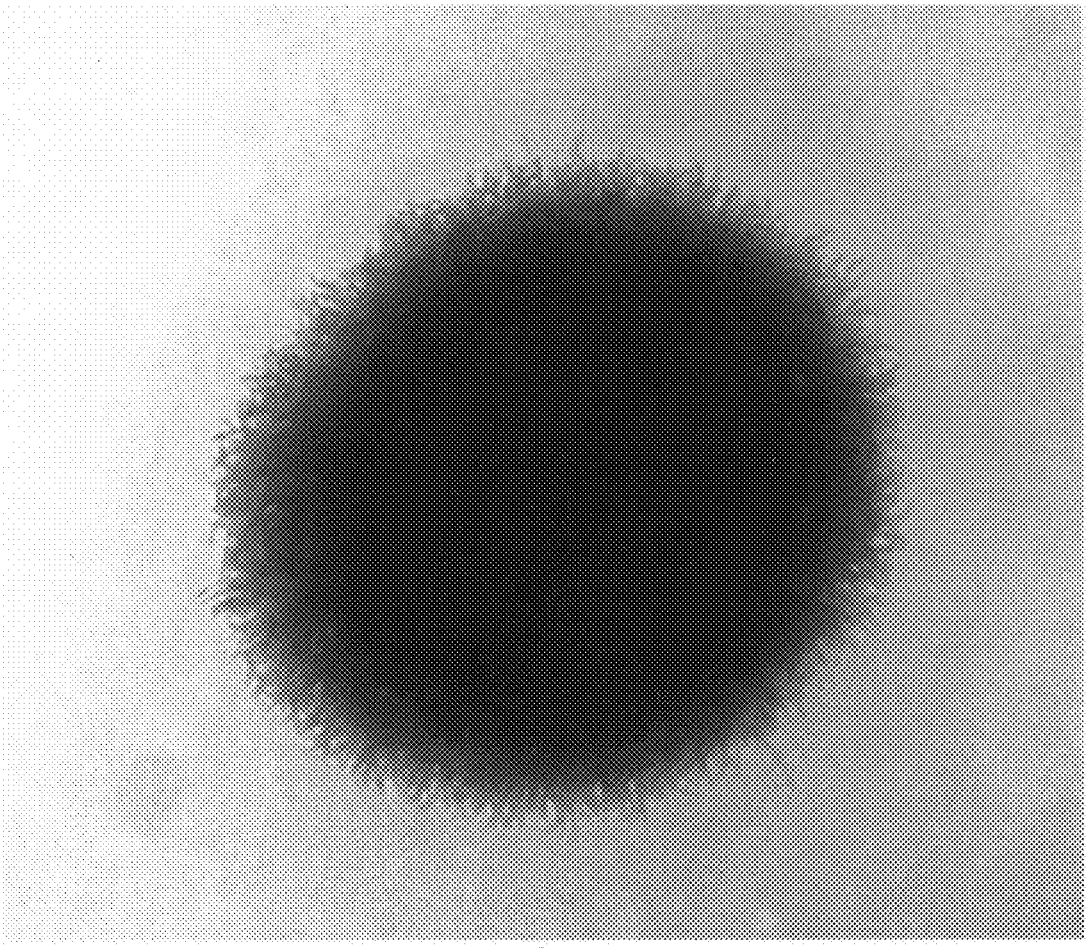

Latin name of the genus and species: *Asparagopsis taxiformis*.

Variety denomination: "Icarus".

BACKGROUND

Globally, livestock methane emissions contribute about 10% of total global greenhouse gas (GHG) emissions. While many have highlighted solutions to address emissions from other sectors, there is a gap in applicable and effective approaches to addressing livestock emissions. The red macroalgae *Asparagopsis taxiformis* as a livestock feed supplement has the potential to drastically decrease this source of emissions. At a 0.5% inclusion rate in ruminant feed, this tropical red seaweed could confer health benefits to cattle while eliminating over 90% of methane emissions.

*A. taxiformis* provides a unique opportunity for high-tech seaweed aquaculture. It is not easily cultivated and has highly impactful end-uses. However, most *A. taxiformis* strains are unable to survive in economical cultivation conditions. For instance, outdoor cultivation of *A. taxiformis* in Hawai'i will require tolerance to peak lighting and heat events.

SUMMARY

The *A. taxiformis* cultivar described herein is a product of a strain selection and cultivation program designed to identify, cultivate, and improve expected strain performance in variable conditions.

Naturally growing *A. taxiformis* were obtained from a rocky intertidal reef shelf in Kailua-Kona, Hawai'i, and were cultivated in growth vessels under high-stress conditions of elevated sea water temperatures (e.g., temperatures of at least 28° C.). In comparison, seawater near Kailua-Kona, Hawai'i typically has a temperature of about 25° C. The temperatures of the growth vessels were controlled using an incubator, and the sterile seawater within was replaced on a weekly basis with a trace metal mixture including zinc (in the form of dissolved $ZnSO_4$ at a range of $5.0\text{-}15.0\times10^{-3}$ ppm by mass), iron (in the form of dissolved $FeCl_3$ at a range of 0.5-1.5 ppm), and vanadium (in the form of dissolved $Na_3VO_4$ at a range of $5.0\text{-}15.0\times10^{-4}$ ppm). Cultivars were grown in the growth vessels and selected for their ability to withstand such elevated seawater temperatures. Due to stress of higher metal inclusions in the initial culture conditions, a spontaneous mutation that was induced in one of the cultivars is believed to have caused the unique morphology and corresponding performance at high temperatures. This process of cultivating *A. taxiformis* was screened over 160 samples, with only one cultivar resulting in abnormal growth with accelerated growth rate under the described conditions. The mutated individual was cultivated repeatedly 5 times and at least for a period of 4 months, with the altered morphology of the described plant maintained.

The progeny of this mutated individual, discovered during experimentation under this program, was named the "Icarus" strain. The strain was able to survive extreme heat events in cultivation conditions. For example, when exposed to 32° C. heat for at least 24 hours, the "Icarus" strain was able to maintain its pigment and displayed almost double the growth rate of the control strains, including wild-type *A. taxiformis*.

The aerial yield of isolated *A. taxiformis* "Icarus" strain described herein, when grown at a temperature of 32° C., was found to be, on average, 280% greater than wild-type *A. taxiformis*. This is particularly interesting, for example, for outdoor, land-based cultivation in tropical climates where *A. taxiformis* can ideally grow. Seasonal temperature fluctuations can cause extreme heating events in algae culture, of which standard cultivated strains of *A. taxiformis* cannot survive. A high temperature strain also may decrease the cost needed for water cooling in tropical climates, which can have a very large cost. As land-based cultivation ponds in areas like Hawai'i regularly peak at temperatures of around 37° C., temperature-resilient strains may become increasingly important to viable land-based cultivation.

At temperatures of about 30° C. or greater, wild-type *A. taxiformis* displays a sharp decline in growth rate, with a lack of cell division and lasting damage marked by distinct pigment loss at the apical cells. Growth cells that display this characteristic loss of pigmentation never resume cell division, and as a result of such heat stress, the plant can never fully resume a commercially productive growth rate. This heat stress can also serve to redirect plant resources away from the production of valuable secondary metabolites, like bromoform, in favor of recovery and growth. Furthermore, heat stress from events like these can allow opportunistic contaminants to outperform *A. taxiformis*, effectively killing off the strain in culture at huge cost during production. In contrast, it has been found that the "Icarus" strain as described herein is able to withstand such temperatures without exhibiting significant damage marked by distinct pigment loss at the apical cells.

BRIEF DESCRIPTION OF THE PHOTOGRAPHS

The accompanying color photographs were taken using methods conventional to microscope photography, and are as accurate as reasonably possible in color given available technology, although the colors may appear slightly different from actual colors, e.g., due to lighting and other variables.

FIG. 1 is a photograph of an "Icarus" cultivar, demonstrating the overall appearance of the plant, including unique traits. This plant is 5 months old and was cultivated in Kailua Kona, Hawai'i. The photo was captured at low magnification to show characteristics of the entire plant. Propagations of this plant maintained this morphology and were tested under a variety of culture conditions to make determinations listed in this description. The diameter of the plant is about 3-4 mm.

Figure 2:
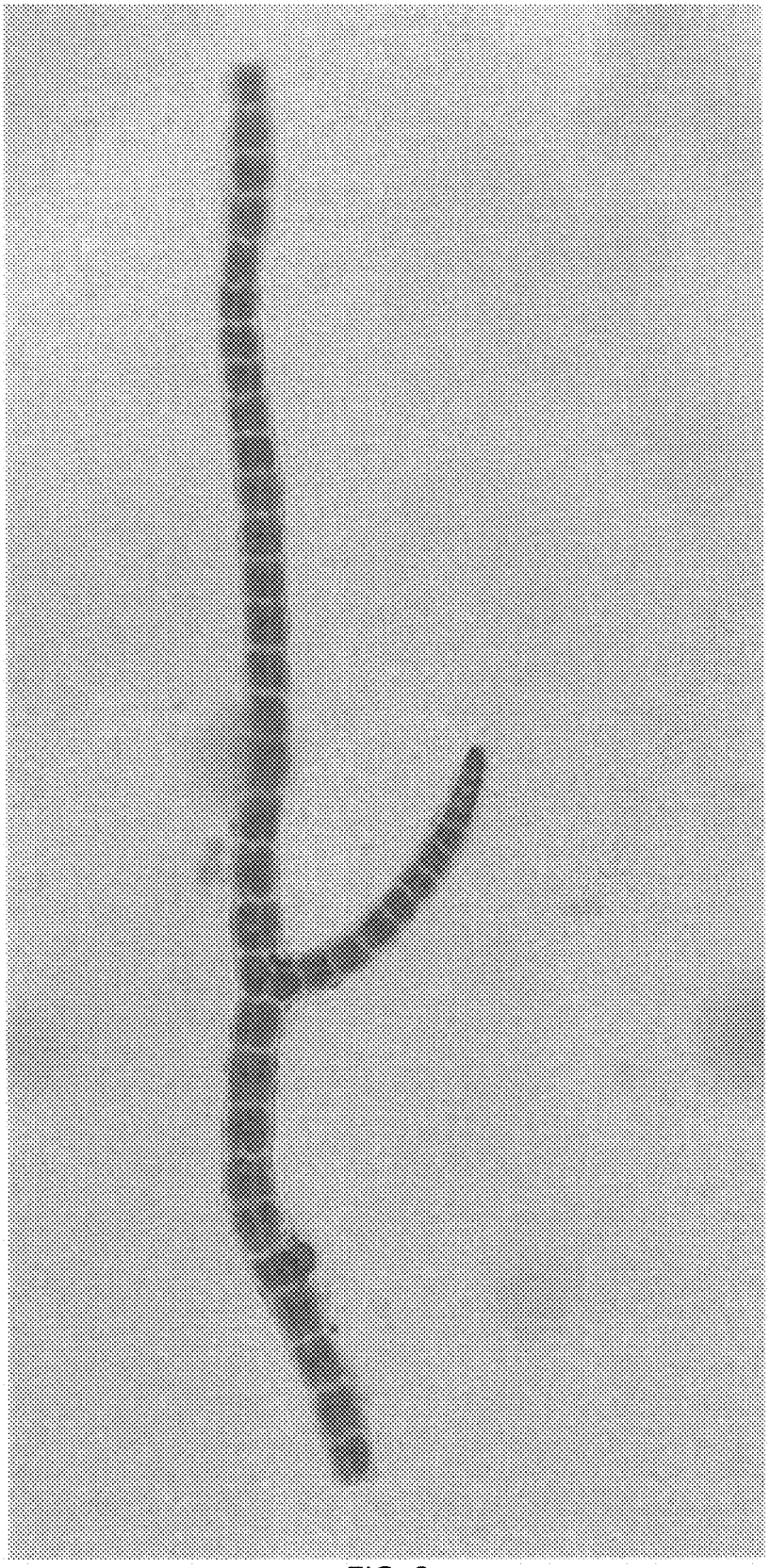

FIG. 2 shows a sample of an "Icarus" cultivar grown from cuttings of collected material sampled from a rocky intertidal reef shelf in Kohala, Hawai'i. The photo was taken at high magnification on a dissection microscope. The whole plant was the same size as the whole plant in FIG. 1, but is shown at an increased magnification to display the specific markers of this plant at a clearer scale. The sample was demonstrated to be stably reproducible, and maintained this unique branch structure after multiple propagations in lab conditions. The estimated age of this tissue is ~2-3 months, based on size and color of the entire plant upon collection. The length of the filament is about 1 mm long.

Figure 3:
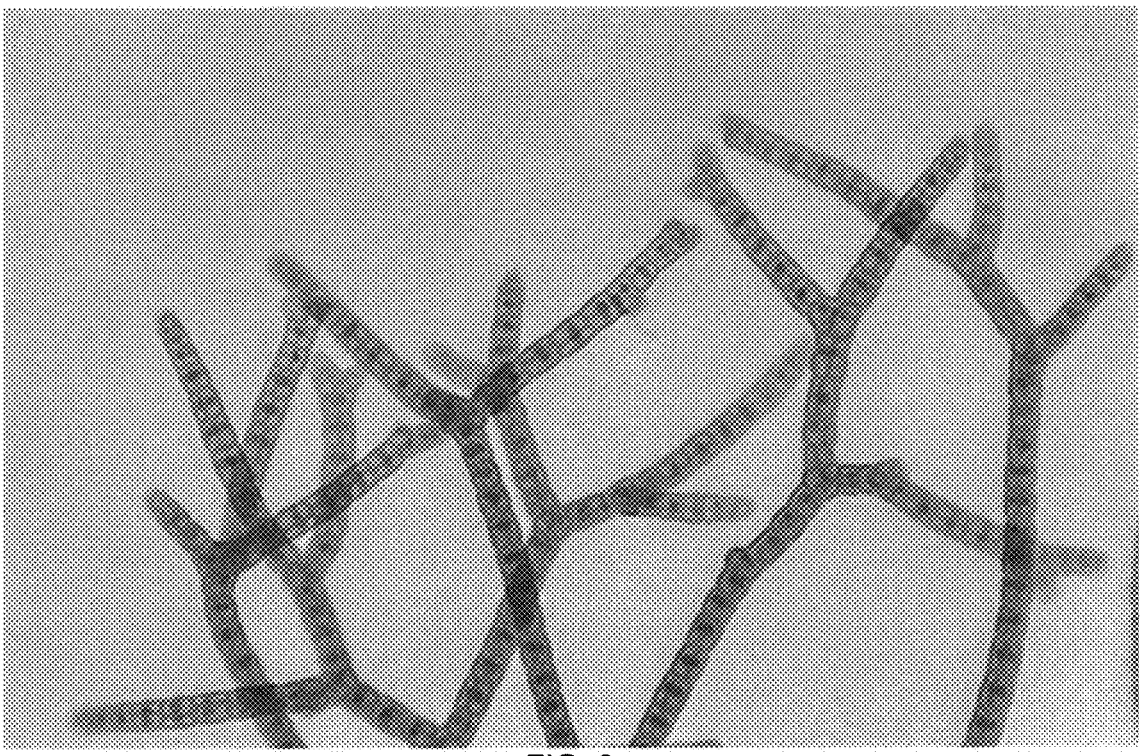

FIG. 3 depicts apical material of a cultivated "Icarus" strain grown in controlled lab conditions in Kailua-Kona, Hawai'i. This clonal tissue was grown from cuttings of collected material sampled from a rocky intertidal reef shelf in Kohala, Hawai'i, and was demonstrated to be stably reproducible. This stable reproduction was demonstrated by targeted fragmentation, in which isolated cell clusters cut from the plant filament were grown and evaluated in enriched sea water under the same conditions as described above (i.e., within growth vessels contained within an incubator at 28° C.). Every month, a cutting from the plant was taken and separately grown in a different growth vessel, and this process repeated over 4 months using the newly grown plant, with the strain exhibiting stable traits as described herein. This method thus showed that the strain was stably asexually reproducible and retained these traits through repeated propagation. The age of the plant in the image is approximately 4 months from cutting. The apical cell division in this plant is much more rounded as compared to what would be expected in wild-type *A. taxiformis*. Notable in this image are the tighter branching, darker pigmentation, rounded tips, and closer shape, as compared to wild-type *A. taxiformis*.

DETAILED BOTANICAL DESCRIPTION

A new and distinct cultivar of the red macroalgae *Asparagopsis taxiformis* named "Icarus," characterized by significantly smaller internal branching angles, a smaller form when aggregated in tumble culture, and a dark purple-red pigmentation, is described herein. New branches of this macroalgae are generated prolifically at higher temperatures than wild-type *A. taxiformis,* making "Icarus" well-suited for commercial growth, e.g., when there is a risk of extreme heat events, in cases of needing to lower the cost of cooling cultivars, or other such conditions.

Wild-type strains of *A. taxiformis* collected from localities with high yearly occurring temperature maxima, like Hawai'i, are generally more predisposed to survival in higher cultivation temperatures, as compared to industry standards in aquaculture. Still, when exposed to temperatures exceeding 28° C., a sharp decline in growth rate is seen as the plant tissue becomes stressed by heat. However, the "Icarus" cultivar does not display this deceleration in growth at 28° C., and instead displays a consistent daily growth rate (DGR) of over 40% in temperatures from 30° C. to 32° C.

The "Icarus" cultivated strain grows in a very densely branched tuft morphology (e.g., as shown in FIG. 1), and maintains a high growth rate in temperatures of 30° C. or more. In all tested temperatures and growth conditions, the "Icarus" strain maintained characteristics such as the following:

1. Close branching distinguished by a shorter distance between each new branch.
2. A smaller angle from main branch to new growth (having an average angle of around 65°).

3. Dark wine red pigmentation of established plant (#60A, based on the 2015 edition of The Royal Horticultural Society Colour Chart).
4. Oblong apical cell arrangement as opposed to more conical shape in wild-type strains.

In the wild, higher temperature conditions are often also high sun conditions, for example a tetrasporophyte growing on a rock in the intertidal zone. The "Icarus" strain exhibits a distinctive branching pattern that is significantly more compact than wild-type strains, and without wishing to be bound by any theory, it is believed that this distinctive branching pattern may allow the strain to self-shade from the sun, which may allow it to outperform wild-type strains.

In addition, the distinctive branching pattern of the "Icarus" strain has a lower surface-area-to-volume ratio, as compared to the structure of wild-type *A. taxiformis*. This distinctive compact branching pattern may also help to shield interior cells from temperature fluctuations, which may allow the "Icarus" strain to maintain a high growth rate at higher temperatures. In contrast, when cultivated in high lighting conditions, wild-type strains of *A. taxiformis* will display a lightening in pigmentation, as photoinhibition prevents cellular processes associated with photosynthesis from occurring.

After isolating the germplasm from the "Icarus" strain, propagated clones were analyzed in identical growth conditions for validation of target traits. Every replicate of the "Icarus" strain that was tested displayed a similar increased growth rate, and maintained characteristics of healthy *A. taxiformis* in temperatures of 32° C., while wild-type strains displayed lightening and other symptoms of heat stress, as discussed above. These experiments also demonstrated that the "Icarus" strain was stable when reproduced by asexual reproduction. Furthermore, it was found that the "Icarus" strain could continue to be propagated even after exposure to temperatures of 32° C. These tests demonstrating the stability of asexual reproduction and the characteristics of the "Icarus" strain were performed in May through August 2021 in Kailua-Kona, Hawai'i.

The following descriptions and color references are based on the 2015 edition of The Royal Horticultural Society Colour Chart except where common dictionary terms are used. The "Icarus" strain has not been observed under all possible environmental conditions. The phenotype may vary somewhat with different environmental conditions, such as temperature, light, salinity, etc., but without any change in the genotype. The following observations and size descriptions are of a cultivated "Icarus" strain grown in controlled lab conditions in Kailua-Kona, Hi. The age of the plant is approximately 4 months from cutting.

Botanical classification: *Asparagopsis taxiformis* "Icarus".

PROPAGATION

Type of propagation typically used: Apical germplasm.
Time to initiate propagation: About 1 day at about 25° C.
Width: 3 cells diameter.
Time to produce a new propagation: About 4 days at about 6 branches.
Stolon description: N/A.
Filament description: Maintains same morphology, branch angle, distance, as parent material.

PLANT DESCRIPTION

Habit: Spherical mass with short, tight branching pattern.
Diameter: Diameter of spherical mass ~6-8 mm.

FILAMENT DESCRIPTION

Cluster description: Exhibits a very tight branching pattern resulting in a unique spherical shape with fewer visible offshoots of filamentous branching.
Branch pattern: New growth on "Icarus" had smaller internal branch angles (mean of 65°) than in wild-type strains.
Pigment: Filaments have darker wine-red shade.
Branch apice: Oblong shape, less conical.
Gland cells: Larger, take up more of the cell by volume than in wild-type strains.
Apical cells: Oblong as compared to what would be expected in wild-type strains.
Diameter of spherical mass of filaments: ~6-8 mm.
Internode length: ~40-50 micrometers.
Tensile strength: 1200-2500 $N/m^2$.
Aspect: Tumble culture.
Texture in water: Spongy.
Texture lyophilized: Fibrous, soft.
Luster: Matte.
Color, when developing: Filaments are slightly lighter in pigment at new cell growth, #62A on The Royal Horticultural Society Colour Chart.
Color, fully developed: Filaments have dark wine-red shade, #60A on The Royal Horticultural Society Colour Chart.

LEAF DESCRIPTION

N/A.

FLOWER DESCRIPTION

N/A.

OTHER CHARACTERISTICS

Disease/pest resistance: Observed resistance to pathogenic bacteria (suspected to be *Streptococcus* spp.), higher than wild-type strains.
Temperature: Observed to tolerate temperature between 15-32° C.

What is claimed is:

1. A new and distinct cultivar of *Asparagopsis taxiformis* named "Icarus" as herein described and illustrated.

* * * * *